(12) United States Patent
Demmer et al.

(10) Patent No.: US 9,895,544 B2
(45) Date of Patent: *Feb. 20, 2018

(54) METHOD FOR CALCULATING AN ESTIMATE OF A TIME-VARYING PHYSIOLOGICAL VARIABLE

(71) Applicant: Medtronic, Inc., Minneapolis, MN (US)

(72) Inventors: Wade M. Demmer, Coon Rapids, MN (US); Troy E. Jackson, Rogers, MN (US); Paul A. Belk, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/382,853

(22) Filed: Dec. 19, 2016

(65) Prior Publication Data

US 2017/0095665 A1 Apr. 6, 2017

Related U.S. Application Data

(63) Continuation of application No. 13/664,544, filed on Oct. 31, 2012, now Pat. No. 9,533,156.

(51) Int. Cl.
*A61N 1/36* (2006.01)
*A61N 1/362* (2006.01)
(Continued)

(52) U.S. Cl.
CPC .......... *A61N 1/3621* (2013.01); *A61B 5/0031* (2013.01); *A61B 5/0422* (2013.01); *A61B 5/0456* (2013.01); *A61B 5/4836* (2013.01); *A61M 5/142* (2013.01); *A61M 5/1723* (2013.01); *A61N 1/365* (2013.01); *A61N 1/3684* (2013.01); *A61N 1/3962* (2013.01); *G06F 19/3468* (2013.01)

(58) Field of Classification Search
CPC ..................... A61N 1/36514; A61N 1/36585
See application file for complete search history.

(56) References Cited

U.S. PATENT DOCUMENTS

| | | | |
|---|---|---|---|
| 4,969,465 | A | 11/1990 | Pless et al. |
| 5,987,356 | A | 11/1999 | DeGroot |

(Continued)

FOREIGN PATENT DOCUMENTS

| | | | |
|---|---|---|---|
| EP | 956092 | B1 | 11/1999 |
| EP | 957984 | B1 | 11/1999 |
| EP | 1015073 | B1 | 7/2000 |

*Primary Examiner* — Amanda Patton

(57) ABSTRACT

A medical device performs a method for computing an estimate of a physiological variable. The method includes sensing a physiological signal and measuring an event of the physiological signal. The device initializes a value of a long-term metric of the event measurement, wherein the long-term metric corresponds to a time interval correlated to a response time of the physiological variable to changes in the event. The estimate of the long-term metric is updated in a memory of the medical device using a previous long-term metric and a current measurement of the event. The device detects a need for computing the physiological variable and computes an estimate of the physiological variable using the updated long-term metric.

16 Claims, 5 Drawing Sheets

(51) Int. Cl.
*A61B 5/00* (2006.01)
*A61B 5/042* (2006.01)
*A61B 5/0456* (2006.01)
*A61N 1/365* (2006.01)
*A61N 1/368* (2006.01)
*A61N 1/39* (2006.01)
*A61M 5/172* (2006.01)
*A61M 5/142* (2006.01)
*G06F 19/00* (2018.01)

(56) References Cited

U.S. PATENT DOCUMENTS

| | | |
|---|---|---|
| 6,748,272 B2 | 6/2004 | Carlson et al. |
| 7,047,015 B2 | 5/2006 | Hawe |
| 7,177,683 B2 | 2/2007 | Belk |
| 7,308,305 B1 | 12/2007 | Province et al. |
| 7,532,929 B2 | 5/2009 | Mussig et al. |
| 7,640,054 B2 | 12/2009 | Koyrakh et al. |
| 7,933,650 B2 | 4/2011 | Li |
| 7,991,471 B2 | 8/2011 | Ghanem et al. |
| 8,046,065 B2 | 10/2011 | Burnes et al. |
| 9,533,156 B2 * | 1/2017 | Demmer ............... A61N 1/365 |
| 2007/0191894 A1 | 8/2007 | Li |
| 2008/0114411 A1 | 5/2008 | Lian et al. |
| 2011/0172727 A1 | 7/2011 | Ousdigian |

* cited by examiner

METHOD FOR CALCULATING AN ESTIMATE OF A TIME-VARYING PHYSIOLOGICAL VARIABLE

This application is a continuation of U.S. patent application Ser. No. 13/664,544, filed Oct. 31, 2012, the entire content of which is incorporated herein by reference.

TECHNICAL FIELD

The disclosure relates generally to medical devices and, in particular, to an apparatus and method for calculating an estimate of a physiological variable.

BACKGROUND

Implantable medical devices (IMDs) such as pacemakers and implantable cardiovertor defibrillators (ICDs) typically include sensors for monitoring physiological signals from a patient, such as cardiac electrodes for sensing cardiac electrogram (EGM) signals. Using the sensed signals, the IMD may be configured to compute measurements corresponding to a patient's cardiac rhythm and use that information in computing therapy parameters controlling an automatically delivered therapy, such as a cardiac pacing therapy, which may be a single chamber, dual chamber or multi-chamber cardiac resynchronization therapy (CRT), anti-tachycardia pacing (ATP) or other pacing therapies.

In some examples, control parameters determined from a sensed signal may be computed from measurements of a physiological variable taken over a relatively short period of time, such as one cardiac cycle or several cardiac cycles. In other examples, a parameter may be desired which requires computation from a physiological variable that requires measurements over a relatively longer period of time, such as one minute, several minutes, hours, weeks or more. A relatively large amount of IMD memory is required for storing signal data as it is acquired for use in computing of a physiological variable using long-term measurements of a physiological signal. Computing a time varying physiological variable from signal measurements may require complex computational methods, such as differential, exponential, logarithmic or other non-linear functions, which require generally high processing power and time. Computation of therapy control parameters using measurements obtained over long time periods and/or requiring high computational complexity can be limited in an IMD because of the overall size limitations, which limits battery size, memory size, and processing power. A need remains, therefore, for IMD systems and associated methods that provide efficient computation of an estimated or predicted value of a physiological variable for use in setting a therapy control parameter and/or for assessing a patient condition.

DETAILED DESCRIPTION

In the following description, references are made to illustrative embodiments. It is understood that other embodiments may be utilized without departing from the scope of the disclosure.

Figure 1:
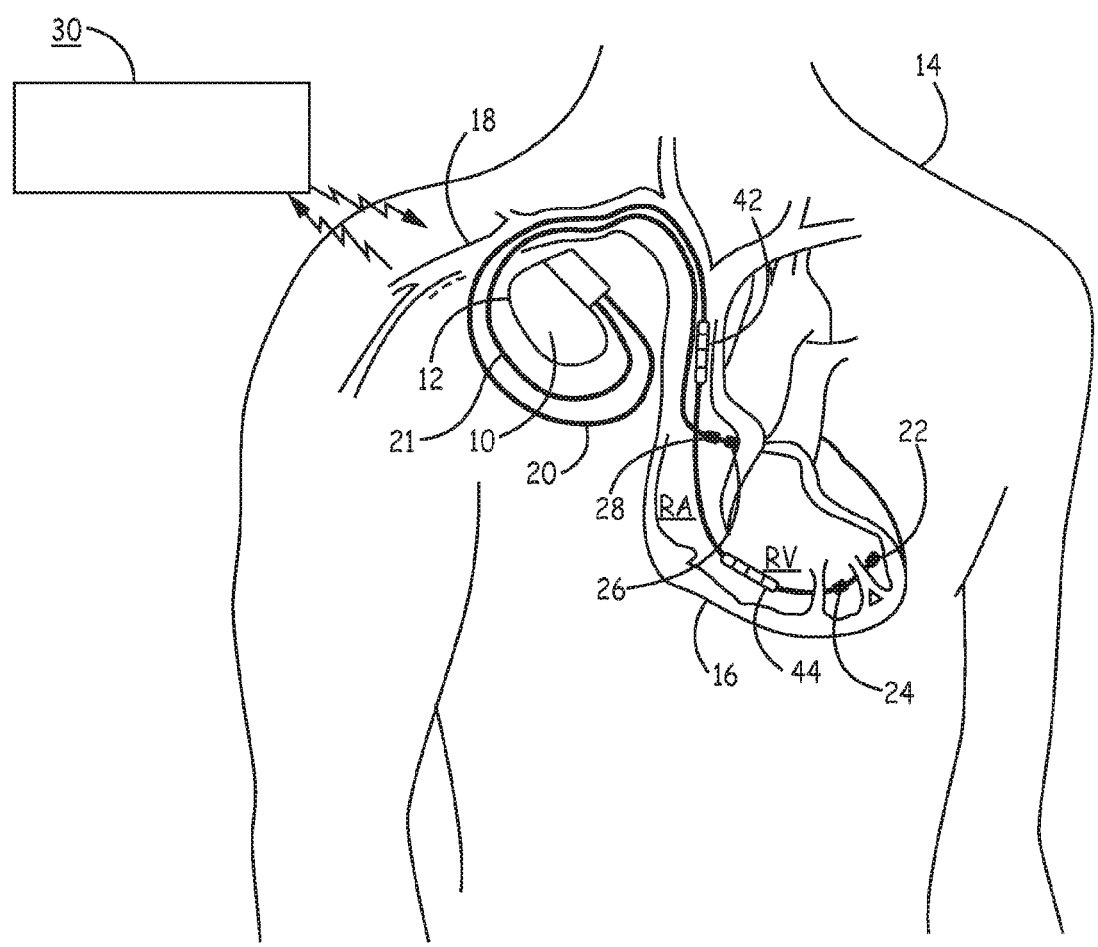
FIG. 1 is a schematic diagram of an implantable medical device system 8 according to one embodiment.

FIG. 1 is a schematic diagram of an implantable medical device system 8 according to one embodiment. System 8 is provided for sensing cardiac events (e.g. P-waves and R-waves) for detecting and classifying a cardiac rhythm and for treating cardiac arrhythmias. System 8 includes IMD 10 and leads 20 and 21. IMD 10 may be embodied as an ICD capable of delivering pacing, cardioversion and defibrillation therapy to the heart 16 of a patient 14. Ventricular lead 20 and atrial lead 21 are electrically coupled to IMD 10 and extend into the patient's heart 16 via a vein 18. Ventricular lead 20 includes electrodes 22 and 24 shown positioned in the patient's right ventricle (RV) for sensing ventricular EGM signals and for delivering pacing pulses in the RV. Atrial lead 21 includes electrodes 26 and 28 positioned in the patient's right atrium (RA) for sensing atrial EGM signals and delivering pacing pulses in the RA. Lead 20 additionally carries high voltage coil electrodes 42 and 44 used to deliver cardioversion and defibrillation shock pulses.

The leads 20 and 21 are used to acquire intracardiac EGM signals from the patient 14 and to deliver therapy in response to the acquired data. IMD 10 is shown as a dual chamber ICD, but in some embodiments, system 8 may be embodied as a single chamber system or as a multi-chamber system including a coronary sinus lead extending into the right atrium, through the coronary sinus and into a cardiac vein to position electrodes along the left ventricle (LV) for sensing LV EGM signals and delivering pacing pulses to the LV.

IMD circuitry configured for performing the methods described herein and associated battery(ies) are housed within a sealed housing 12. Housing 12 may be conductive so as to serve as an electrode for use as an indifferent electrode during pacing or sensing or as an active electrode during defibrillation. As such, housing 12 is also referred to herein as "housing electrode" 12.

EGM signal data, cardiac rhythm episode data, and therapy delivery data acquired by IMD 10 can be transmitted to an external device 30. External device 30 may be embodied as a programmer, e.g. used in a clinic or hospital to communicate with IMD 10 via wireless telemetry. External device 30 may be coupled to a remote patient monitoring system, such as Carelink®, available from Medtronic, Inc., Minneapolis, Minn. Device 30 is used to program commands or operating parameters into IMD 10 for controlling IMD function and to interrogate IMD 10 to retrieve data, including device operational data as well as physiological data accumulated in IMD memory. Examples of communication techniques used by IMD 10 and external device 30 include low frequency or radiofrequency (RF) telemetry, which may be an RF link established via Bluetooth, WiFi, or MICS, for example.

The techniques disclosed herein are useful in IMD system 8, for example, in computing pacing control parameters such as anti-tachycardia pacing (ATP) interval used to control pacing delivered to terminate ventricular or atrial tachycardia. System 8 is one example of an IMD system used to acquire physiological signals, in this example cardiac EGM signals, for measuring physiological variables that are used to set adjustable therapy control parameters to a value computed based on the measured physiological variables in a closed-loop, automatic therapy delivery system. However, the techniques disclosed herein may be implemented in any medical device system that senses physiological signals for use in calculating and reporting a time-varying physiological variable or for calculating a physiological variable used to compute a therapy delivery control parameter. Such systems may include but are not limited to cardiac monitors, respiration monitors, drug delivery devices, and neurostimulation devices. Systems employing the techniques described herein may be wholly external systems or may include implantable devices as shown in the illustrative embodiments.

Figure 2:
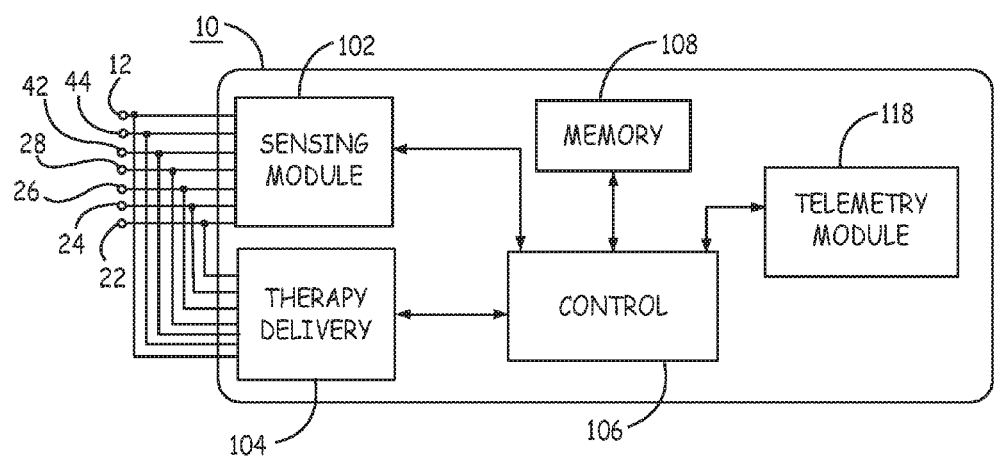
FIG. 2 is a functional block diagram of the IMD shown in FIG. 1 according to one embodiment.

FIG. 2 is a functional block diagram of IMD 10 according to one embodiment. IMD 10 includes a sensing module 102, a therapy delivery module 104, a control unit 106 and associated memory 108, and telemetry module 118. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Sensing module 102 receives cardiac electrical signals from electrodes carried by leads 20 and 21 for sensing cardiac events attendant to the depolarization of myocardial tissue, e.g. P-waves and R-waves. Sensing module 102 may include a switch module for selectively coupling electrodes 22, 24, 26, 28, 42, 44, and housing electrode 12 to sensing module 102 in order to monitor electrical activity of heart 16. The switch module may include a switch array, switch matrix, multiplexer, or any other type of switching device suitable to selectively couple electrodes to sensing module 102. In some examples, control unit 106 selects the electrodes to function as sense electrodes, or the sensing vector, via the switch module within sensing module 102.

Sensing module 102 may include multiple sensing channels, each of which may be selectively coupled to respective combinations of electrodes 22, 24, 26, 28, 42, 44 and housing 12 to detect electrical activity of a particular chamber of heart 16, e.g. an atrial sensing channel and a ventricular sensing channel. Each sensing channel may comprise a sense amplifier that outputs an indication to control unit 106 in response to sensing of a cardiac depolarization, in the respective chamber of heart 16. In this manner, control unit 106 may receive sense event signals corresponding to the occurrence of sensed R-waves and P-waves in the respective chambers of heart 16. Sensing module 102 may further include digital signal processing circuitry for providing control unit 106 with digitized EGM signals, which may be used for cardiac rhythm discrimination and for computing physiological variable values for adjusting therapy control parameters.

Sensing module 102 is shown coupled to electrodes for sensing cardiac EGM signals in FIG. 2. In other embodiments, however, electrodes for sensing other neurological signals and/or other physiological sensors may be coupled to sensing module 102. Other physiological sensors may include pressure sensors, oxygen sensors, pH sensors or other blood chemistry sensors, accelerometers, acoustical sensors, impedance sensors, flow sensors, or any other sensors used for acquiring physiological signals over time.

Any physiological signals received by sensing module 102 and acquired by IMD 10 may be used in the techniques described herein for estimating a physiological variable that varies in response to a changing physiological condition(s), monitored by sensing module 102. In an illustrative embodiment described herein, myocardial action potential duration (APD) varies with heart rate, i.e. RR interval. The faster the heart rate (shorter RRI), the shorter the APD, and the slower the heart rate (longer RRI) the longer the APD. However this variation of APD does not occur suddenly with changes in RRI but changes differentially toward a stable setpoint over time. The APD can be accurately computed as the solution of a finite difference equation which is a function of the RRIs. This accuracy, however, is at the cost of increased memory requirements for storing RRIs over an extended period of time, e.g. one minute or more, or of a higher processing demand and time for computations.

By using a hierarchy of computationally simpler metrics, for example a simple metric of the long-term RRI behavior, and a perhaps more sophisticated metric of the medium and/or short term RRI behavior, a good approximation of the differential behavior of the APD based on heart rate history can be computed with reduced cost. This approximation could require negligible processing time and substantially reduced memory. The approximation can be computed on demand when a need for therapy is detected without requiring continuous computations when a therapy is not needed.

Techniques described herein enable efficient data storage and computational methods for estimating a physiological variable, e.g. APD, based on a time-varying physiological condition or repeating events, e.g. RRI. From the physiological variable, e.g. APD, a therapy control parameter, e.g. a cardiac pacing interval, can be computed. In various embodiments, the techniques described herein may be used for estimating any physiological variable that is challenging to measure directly or instantaneously for use in monitoring a patient or controlling a therapy. The variable may change in response to another physiological condition in a non-linear manner. The variable therefore is estimated using measurements of at least one time-varying physiological condition or repeating event that influences the variable over time and which can be measured from signals sensed by sensing module 102.

Memory 108 may include computer-readable instructions that, when executed by control unit 106, cause IMD 10 to perform various functions attributed throughout this disclosure to IMD 10 and control module 106. The computer-readable instructions may be encoded within memory 108. Memory 108 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Control unit 106 may include any one or more of a microprocessor, a controller, a digital signal processor (DSP), an application specific integrated circuit (ASIC), a field-programmable gate array (FPGA), or equivalent discrete or integrated logic circuitry or state machine. In some examples, control unit 106 may include multiple components, such as any combination of one or more microprocessors, one or more controllers, one or more DSPs, one or more ASICs, or one or more FPGAs, as well as other discrete or integrated logic circuitry or state machines. The functions attributed to control unit 106 herein may be embodied as software, firmware, hardware or any combination thereof.

Control unit 106 includes a therapy control unit that controls therapy delivery module 104 to deliver electrical stimulation therapy, e.g., cardiac pacing, anti-tachyarrhythmia therapy, or shock pulses, to heart 16 according to a selected one or more therapy programs, which may be stored in memory 108. Therapy delivery module 104 is electrically coupled to electrodes 22, 24, 26, 28, 42, 44 and housing electrode 12 (all of which are shown in FIG. 1). Therapy delivery module 104 is configured to generate and deliver electrical stimulation therapy to heart 16 via selected combinations of electrodes 22, 24, 26, 28, 42, 44, and housing electrode 12.

Memory 108 stores intervals, counters, or other data used by control unit 106 to control the delivery of pacing pulses by therapy delivery module 104. Such data may include intervals and counters used by control unit 106 to control the delivery of pacing pulses to heart 16. The intervals and/or counters are, in some examples, used by control unit 106 to control the timing of delivery of pacing pulses relative to an intrinsic or paced event in another chamber. Memory 108 also stores intervals for controlling cardiac sensing functions such as blanking intervals and refractory sensing intervals and counters for counting sensed events for detecting cardiac rhythm episodes. Events sensed by sense amplifiers included in sensing module 102 are identified in part based on their occurrence outside a blanking interval and inside or outside of a refractory sensing interval. Events that occur within predetermined interval ranges are counted for detecting cardiac rhythms.

Memory 108 is additionally used to store data used for computing an estimate of a physiological variable and optionally for computing a therapy control parameter using the physiological variable. According to one embodiment described herein, sensing module 102, memory 108, and control unit 106 are configured to measure a current value of a repeating physiological event or condition, use the current value to update a long-term metric of the physiological condition, and store the long-term metric of the condition. At a time that therapy is needed, as determined by control unit 106 based on sensed signals from sensing module 102, the long-term metric is used to compute an estimate of a physiological variable that varies in response to changes in the physiological condition. A therapy control parameter is then computed based on the estimated physiological variable. Next, the therapy control parameter is applied by control unit 106 to control therapy delivered by therapy delivery module 104.

Telemetry module 118 is used to communicate with external device 30, for transmitting data accumulated by IMD 10 and for receiving interrogation and programming commands from external device 30. Examples of communication techniques used by IMD 10 include low frequency or radiofrequency (RF) telemetry, which may be an RF link established via Bluetooth, WiFi, or MICS. IMD 10 receives programming commands and algorithms from an external device via telemetry module 118.

Figure 3:
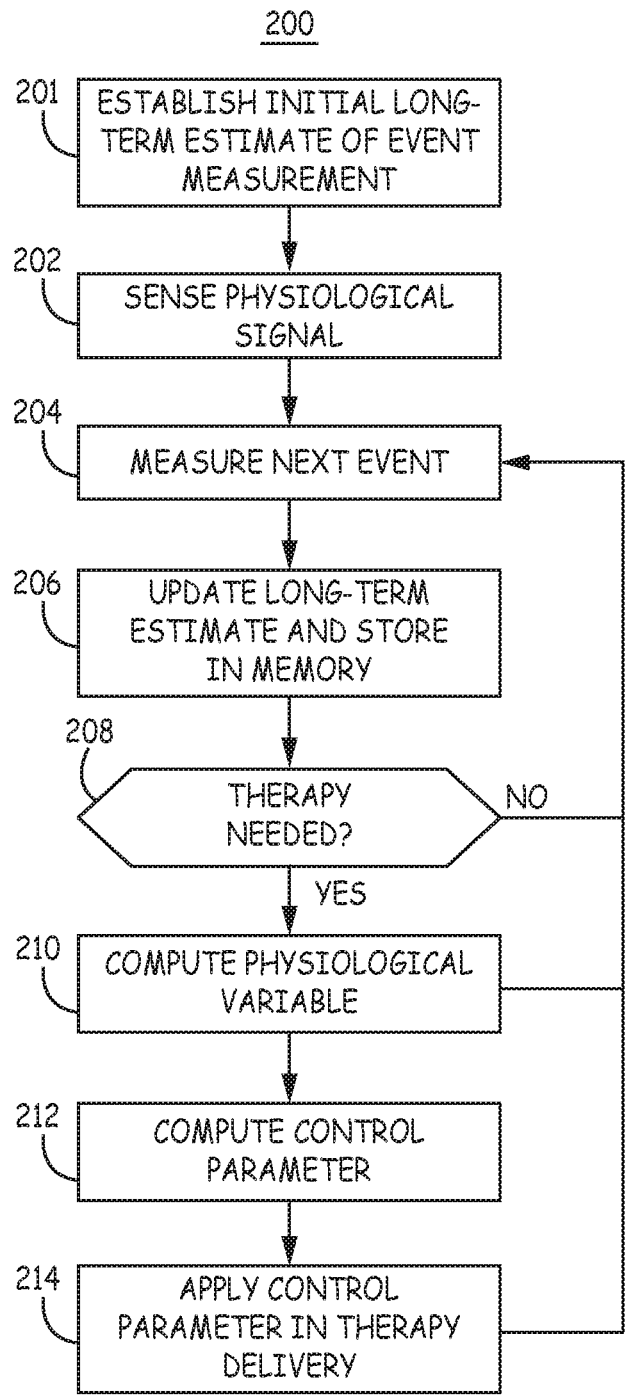
FIG. 3 is a flow chart of a method for computing a therapy control parameter according to one embodiment.

FIG. 3 is a flow chart 200 of a method for computing a therapy control parameter according to one embodiment. Flow chart 200 and other flow charts presented herein are intended to illustrate the functional operation of the medical device system, and should not be construed as reflective of a specific form of software or hardware necessary to practice the methods described. Methods described in conjunction with flow charts presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

At block 201, an initial estimate of a long-term metric of a physiological condition is established. A long-term metric may be any statistical metric of measurements of a physiological condition. For example, a long-term metric may be a mean (average), median, mode or other measurement of the central tendency of a distribution of measurements of the physiological condition obtained from a sensed signal. The initialized estimate of the long-term metric is stored in memory 108. Examples of physiological conditions that may be measured include, but are not limited to, cardiac conditions, metabolic conditions and respiratory conditions. The measurement of the condition may be an amplitude, a time interval, a slope, an integral, a dose, a waveform morphology, or other aspect of the physiological signal.

The physiological condition may be any event for which repeated measurements are obtained and may be a cyclical event, such as a cardiac event, respiratory event, or circadian event. To illustrate, a repeating event may be an RR interval (RRI) measured as the interval between R-waves consecutively sensed from a cardiac EGM signal. An initial long-term estimate of a central tendency or "centeredness" of the RRI distribution may be an average RRI initialized as a currently measured RRI, a short-term average, e.g. a five to ten beat average, or a nominal RRI value.

At block 202, the physiological signal used to measure the physiological condition is sensed by the IMD. The next measurement of the physiological event is performed at block 204. This measurement may be of the next occurrence of a repeating event. At block 206, the long-term estimate of the metric of the physiological condition is updated using the next measurement and the new long-term estimate is stored in memory 108. The actual value of the current event measurement does not need to be accumulated in memory 108. In contrast to methods that accumulate measurements of a physiological condition or repeating event over time to enable computation of a long-term average or other measure of centeredness of the repeating measurements, only the updated long-term estimate needs to be stored at block 206, significantly reducing memory requirements.

The "long-term" metric refers to a metric correlated to the central tendency of the physiological condition over a period of time corresponding to a response time of a physiological variable to changes in the condition. An example of this relation is the APD that changes differentially with changes in RR interval. The response time of APD to changes in RR interval may be on the order of approximately one minute such that a long-term metric of RR interval is intended to correlate to a one-minute average RR interval in one embodiment, without having to store one minute of RR interval measurements.

At block 208, the IMD control unit 106 determines if a therapy is needed. This determination may be made according to any detection algorithm implemented in the IMD 10 for detecting a need for therapy. Examples include cardiac event interval tachyarrhythmia detection algorithms, which may utilize a prioritized set of rules, event patterns, signal morphology criteria or other detection criteria in addition to measurements and counts of RR and/or PP, and PR intervals for detecting tachyarrhythmias.

If no condition or episode is detected by the IMD requiring therapy at block 208, the control unit 106 continues to measure the physiological condition at block 204 and updating the long-term estimate of the physiological condition at block 206, which is stored in memory.

If therapy is needed (block 208), a physiological variable is computed at block 210 upon demand for use in controlling the therapy. The physiological variable is a variable that depends on the long-term behavior of the physiological condition, which may be a repeating event, and therefore cannot be computed from only a currently measured value or a relatively short-term measurement of the physiological condition. Normally, a large amount of memory and processing would be required to compute the physiological variable from a large amount of accumulated event measurements. Instead, upon determining that a therapy is needed, an estimate of the physiological variable is computed using the long-term metric of the physiological condition. Additionally a current value of the condition measurement and/or another short- or medium-term measurement of the condition may be used in the computation of the physiological variable to estimate the variable as a function of the physiological condition.

At block 212, a therapy control parameter that is automatically adjusted as a function of the physiological variable is computed by the control unit 106. The therapy control parameter is applied by the therapy control portion of control unit 106. Therapy is applied according to the control parameter at block 214. After delivering the therapy, the process may return to block 204 to continue measuring the physiological event and updating the long-term metric of the event.

In some cases, the therapy is an urgent therapy, such as a tachyarrhythmia therapy, and accordingly minimum processing time for computing a therapy control parameter is desired. By storing a long-term metric of the physiological condition needed to compute an estimate of the physiological variable, processing time for computing the therapy control parameter upon detecting a need for therapy is minimized, enabling prompt therapy delivery.

As will be described in an illustrative embodiment below, a pacing interval used for delivering ATP in response to detecting a tachycardia episode may be computed as a function of an estimate of APD. In one embodiment, the APD is estimated using a long-term metric of the RRI. Accordingly, upon detecting a need for ATP, the pacing interval can be computed on demand using the long term metric of the RRI for estimating the APD, which in turn is used to compute the ATP interval. While the estimated APD may be somewhat less accurate than an action potential duration computed using the full computational method of differentially processing all RRI measurements accumulated and stored over a long-term interval, the efficiency gained in reducing processing time and memory requirements by using the updated long-term metric of RRIs provides a more feasible technique for implementation in an IMD system.

In some embodiments, the estimated physiological variable itself may be stored and reported as part of a monitoring algorithm. In this case, the physiological variable estimate may be computed on a periodic basis and stored in memory 108 or on demand, e.g. in response to an interrogation command from programmer 30, and transmitted via telemetry module 118. A therapy control parameter need not be computed in all applications of the disclosed techniques; in some embodiments an estimated physiological variable is computed, from a long-term metric of a repeating physiological event or condition that influences the variable, for patient monitoring purposes, without therapy delivery.

Figure 4:
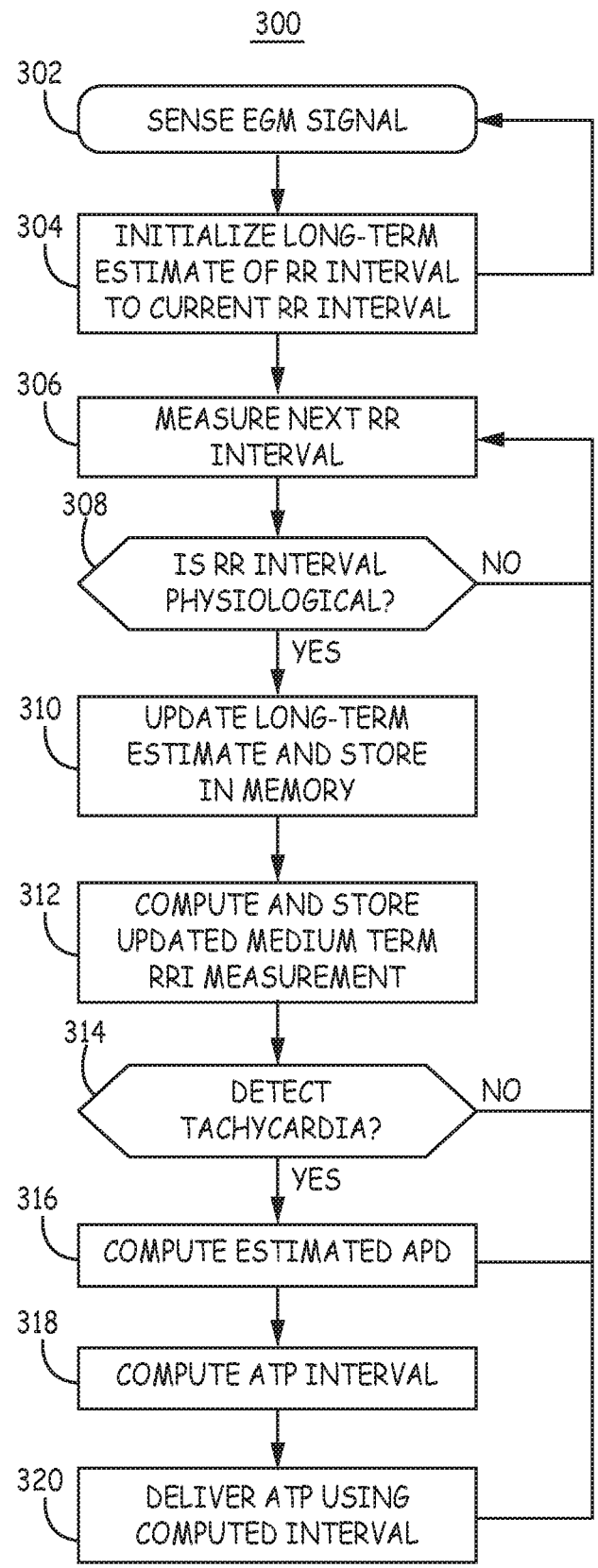
FIG. 4 is a flow chart of one method for computing a therapy control parameter according to an illustrative embodiment.

FIG. 4 is a flow chart 300 of one method for computing a therapy control parameter according to an illustrative embodiment. At block 302, an EGM signal is sensed. For example a ventricular EGM signal is sensed using electrodes 22 and 24. At bock 304, a current RRI is measured. A long-term metric of an average RRI is initialized to the current RRI value.

At block 306, the next RRI is measured. The next RRI is compared to a predefined physiological limit or range of RRIs at block 308. In one embodiment, the RRI is required to be greater than a minimum RRI limit, for example greater than 150 ms. If the next RRI is not determined to be physiological based on predetermined acceptability criteria, the next RRI is measured at block 306. In some cases, non-cardiac noise or oversensing of signals that are not true R-waves may cause false R-wave detections resulting in non-physiological RRI measurements. These non-physiological RRI measurements are rejected for use in updating an estimate of the long-term average RRI.

The next RRI measurement that is determined to be physiological is used, along with the initialized long-term metric, to update the metric of the long-term average RRI at block 310. An updated metric of a long-term average may be computed by the control unit 106 as a weighted sum of the stored metric of the long-term average and the currently measured RRI. In one embodiment, the metric is computed as:

$$\text{LTAvg(updated)}=\{(n-1)*\text{LTAvg}\}/n+\text{RRI}/n$$

wherein LTAvg is the stored long-term average estimate, RRI is the currently measured RRI value, and n is a selected weighting factor. The weighting factor n is chosen to be 256 in one embodiment. The weighting factor may be selected based on a fastest event rate expected to occur over a time interval needed to accurately estimate the physiological variable. In other words, the weighting factor may be established based on an expected number of event measurements during a response time of the physiological variable to changes in the event. The long-term metric is correlated to a centeredness measurement of the event over the response time in one embodiment. Additionally, the weighting factor may be selected to enable straightforward hardware or firmware implementation in fixed point math.

For example, the APD may be estimated with an acceptable accuracy based on approximately one minute of RRI measurements. Approximately one minute may include between 50 seconds and 70 seconds of measurements for example. During a fast heart rate, the tachycardia rate may be greater than 200 bpm, normally requiring storage of the 200 or more RRIs to determine an average RRI from which the APD could be computed. Instead of requiring this large amount of data storage, only the long-term metric of average RRI is stored and a currently measured RRI is used to update the metric. A maximum event rate in an expected time interval required to estimate APD with acceptable accuracy may be set at a rate greater than approximately 200 bpm, corresponding to an expected maximum ventricular rate during the one minute time interval used to estimate APD. In the illustrative embodiment, a maximum event rate is selected as 256, since this rate is close to an expected maximum ventricular rate if VT is detected, is computationally convenient to use in hardware/firmware implementations, and provides an acceptable resolution of a final APD estimate.

This established maximum event rate is used to set the weighting factor applied to the long-term metric and the currently measured RRI. A weighting of 255 is applied to the long-term metric and a weighting of one is applied to the currently measured RRI in computing the updated metric of long-term average RRI over an assumed maximum number of events, i.e. 256. For example, for computing the metric of the long-term average RRI the following equation may be used:

$$LTAvg(updated)=\{(255)*LTAvg\}/256+RRI/256$$

The above equation may be generalized to a long-term average metric of any repeated event measure where the long-term average (or other centeredness) metric is updated as a sum of a weighted combination of the stored long-term average metric and a current measurement of the repeating event. The weighting factor may be chosen based on modeling of real clinical data to provide a best approximation of the actual long-term average computed from accumulated measurements of a repeating event, e.g. RRIs in the illustrative embodiment. For example, the weighting factor applied to a current event measurement may be higher if a greater dependency on very recent events compared to less recent historical events is observed.

The updated long-term average metric is stored in memory 108 at block 310. The long-term average metric is updated in memory 108 continuously upon each RRI measurement such that every RRI measured (within physiological limits) contributes to the calculation of the historical, long-term average metric. Being continuously updated upon each measurement means that the number of RRI measurements contributing to the long-term average metric is not limited to a predetermined number of RRIs and RRIs need not be counted for computing the long-term average. It is recognized that the metric of the long-term average could be reinitialized, for example by a clinician using programmer 30, which would restart computation of the long-term metric, effectively clearing the contribution of historical RRIs to the metric.

A relatively shorter, medium term metric of recent RRIs is computed and stored at block 312. This medium term measure may be a running average, a mean, median, mode or other measure of a predetermined number of the most recent, consecutively measured repeating events, e.g. RRIs (rejecting non-physiological RRIs) in the illustrative embodiment. For example, the median RRI of the most recent 10 or 12 RRIs may be determined and stored at block 312. Generally, the medium term measure could be computed as a mean or median value of a predetermined number of the most recently measured and stored event measurements, but any moment with mathematically desirable properties could be used, and the moment could in general be chosen based on the characteristics of the difference equation being solved.

The number of recent event measurements used to compute the medium term metric may be based on a minimum number of events expected to occur over the time interval required to estimate APD with acceptable accuracy. For example, a minimum heart rate during one minute may be expected to be approximately 40 beats per minute. If the weighting of the long-term average is high, e.g. based on a maximum event rate of 256, but the heart rate is relatively slow or near a minimum expected rate, the long-term metric is heavily weighted on historical RRI values that extend well-beyond the one minute time interval over which RRI changes are expected to impact APD. RRIs occurring more than one minute earlier would have little or no influence on the behavior of the current APD. Accordingly, an estimate of the APD computed using a weighted long-term average metric can be corrected for error arising when a heart rate is slower than a maximum expected rate by determining and appropriately weighting a medium term metric in a computation of APD. A weighted contribution of the medium term metric will be used to offset a long-term metric heavily weighted on historical RRIs in computing the final APD estimate.

In one embodiment, a median value of the most recent 12 RRIs is determined at block 312, and updated beat by beat. This median value requires storage of only 12 RRIs, which generally does not require an excessive amount of memory and is not computationally burdensome to compute. The number of most recent events used to compute a medium term metric may be based on the minimum number of events expected over a time interval required to make event measurements for computing an acceptably accurate estimate of a physiological variable. In other words, the number of most recent events used to compute a medium-term metric may be based on a minimum number of event measurements expected to occur in the response time of the physiological variable to a change in the event. The number of most recent events used may additionally be adjusted from this expected minimum number of events based on available memory capacity, computational convenience, and acceptable accuracy of the estimated APD, which may be based on comparisons to empirical measurements.

The long-term RRI metric and the medium term RRI measurement continue to be updated beat-by-beat until a tachycardia is detected at block 314. The long-term metric is stored without having to accumulate RRI measurements in memory 108 for computing a long-term average RRI. Only the current long-term metric is stored and is updated using a current RRI measurement, resulting in substantial memory and processing savings as opposed to storing all RRIs over a selected time interval, such as one minute, and computing an average of all of those RRIs. Computation of the medium term measure of RRIs does not require a large amount of memory or processing time since only a selected number of the most recent events are used. Accordingly, a predetermined number of recently measured RRIs meeting the physiological interval requirement are stored in a memory buffer to enable computation of the medium-term RRI measurement on a beat-by-beat basis.

If a tachycardia is detected at block 314, an estimated APD is computed at block 316 using the currently stored value for the long-term RRI metric, the medium term RRI metric, and a currently measured RRI. The ventricular refractory period changes as a function of heart rate (RRIs). In order to effectively terminate a detected tachycardia episode using anti-tachycardia pacing (ATP), the ATP pacing pulses must be properly timed. A proper pacing interval will result in a pacing pulse shortly after the ventricular APD and associated physiological refractory period but before the next intrinsic tachycardia depolarization. An ATP therapy will fail to terminate a tachycardia episode when the ATP pulses occur at a time outside of the proper time interval. For example, an ATP therapy applied during the APD will fail to capture the heart due to the physiological refractory period of the myocardial tissue. ATP pulses applied too close to intrinsic tachycardia depolarizations, may accelerate the tachycardia leading to fibrillation. Therefore, the ATP interval may be set based on an estimate of the APD to properly time the pacing pulses just after physiological refractory. Setting the pacing interval of the ATP pulses based on an estimated APD increases the ability of IMD 10 to terminate the detected tachycardia, reducing the likelihood that the tachycardia will degrade into fibrillation, reducing the number of pulses delivered to the patient's heart 16, and increasing the battery life of IMD 10.

The differential behavior of the APD as a function of heart rate can be approximated using a long-term, medium-term, and immediate measure of RRIs. By properly weighting each of the long-term, medium-term and immediate components, a close approximation of the behavior of the APD can be achieved. In one embodiment, the APD is computed on demand at block 314 using a weighted combination of the long-term RRI metric currently stored in memory, a medium-term RRI average currently stored in memory, and the currently measured RRI as follows:

$$APD=MAX(E, C*(S1*LTAvg+S2*MTmedian+S3*RRI_{current})+D)$$

wherein the values S1, S2 and S3 are scaling or weighting factors applied to each of the respective estimated long term average RRI metric (LTAvg), medium term median RRI (MTmedian), and currently measured $RRI_{current}$. C and D are constants. C, S1, S2, S3 and D are selected to provide a best fit approximation of the differential behavior of the APD curve as a function of RRI. C, S1, S2 and S3 can also be selected to provide efficient implementation. In one embodiment, C, S2 and S3 are selected to be 0.25 and S1 is selected to be 0.5. C is a scaling factor that converts the overall RRI metric computed using the long-term, medium term and current RRI metrics to the APD portion of the RRI. S1 is selected to give greater weight to the long-term metric than the medium term metric and the current RRI measurement. However the medium term metric and the current RRI contributions offset any error due to contributions of more distant past historical values.

D is an offset selected as approximately 130 ms, corresponding to a minimum APD and provides a safety margin to ensure pacing outside of the vulnerable period. E is a maximum for the system and is approximately 350 ms in one example. In any given application, the equation used to compute an estimate of a physiological variable may be determined by fitting estimated data to empirical measurements such that selection of scaling factor(s), weighting factors, offset, and a maximum or minimum limit provides acceptable accuracy and resolution of the estimate.

Using the estimated APD based on the metric of the long term RRI and more immediate RRI measurements, a pacing interval for ATP is computed at block 318. The ATP interval may be computed by multiplying the APD by a constant and/or adding a constant to the computed APD. A maximum upper limit to the ATP interval may be set and used in place of a computed ATP interval if it exceeds the maximum limit. The computed ATP interval is used by the therapy control unit included in control unit 106 for controlling therapy delivery unit 104. The ATP therapy is delivered to heart 16 at the computed ATP interval. After delivering the therapy to successfully terminate the detected tachycardia, the process returns to block 306 to continue measuring RRIs on a beat-by-beat basis and updating the long-term RRI metric and the medium term RRI metric.

In other examples, a physiological variable that may be estimated using the techniques disclosed herein may include any variable, e.g. that relating to cardiac function, respiratory function, neurological function, endocrine function, or digestive function, that varies non-linearly in response to changes in a physiological event or condition. A metric of the physiological event or condition is determined over different time intervals including at least one relatively longer time interval. The long time interval metric is estimated using a weighted function of a previous long term estimate and a current measurement of the event or physiological condition. This long-term metric is combined with at least one metric measured or estimated over a relatively shorter time interval, for example a current event measurement and/or a metric of a predetermined number of most recent event measurements. The weighted combination of these metrics is used to approximate the non-linear behavior of the physiological variable that depends on the behavior of the physiological condition or event over a given time interval.

An event or physiological condition measured repeatedly for estimating the long term metric may correspond to cyclical events such as circadian events, respiratory cycles, or cardiac cycles or non-cyclical events such as changes in body fluids, changes in activity, changes in digestive activity etc. The measurement of the event or physiological condition may be an electrical, mechanical (e.g. pressure, acoustical, motion or activity), chemical (e.g. pH, oxygen saturation, or other blood parameters), or optical measurement. The physiological variable estimate may be used for patient monitoring purposes and/or for computing a therapy control parameter as described herein.

Figure 5:
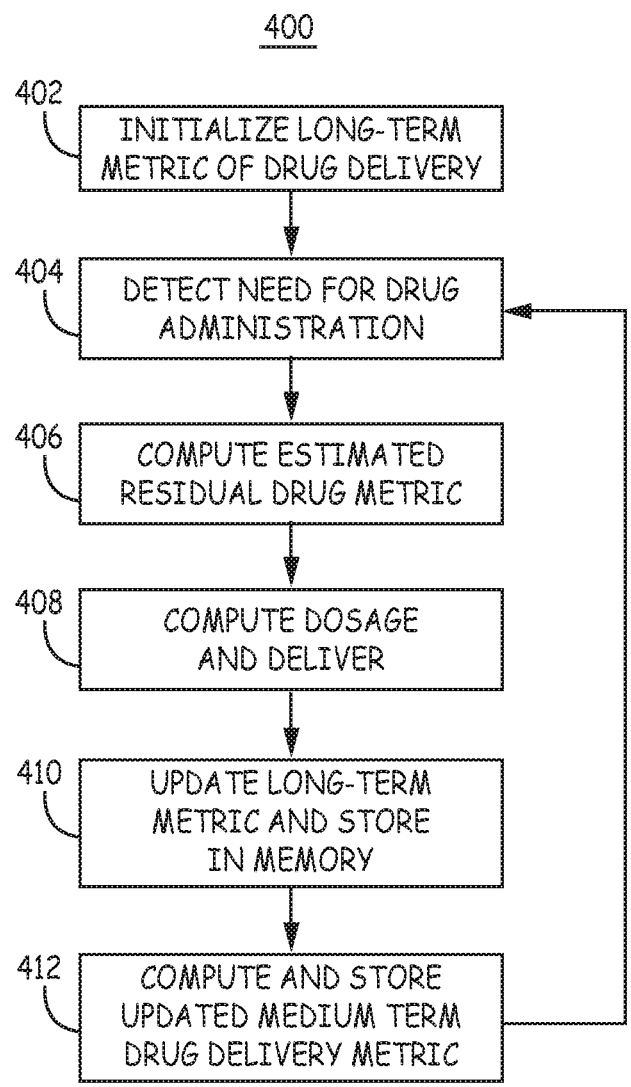
FIG. 5 is a flow chart of a method for controlling a drug therapy using the estimation techniques described herein.

FIG. 5 is a flow chart 400 of a method for controlling a drug therapy using the estimation techniques described herein. If a drug is being administered in response to detecting a pathological event or worsening physiological condition, at equal or varying time intervals and/or dosages, the drug in the patient's system will be present in various pharmacokinetic states corresponding to the uptake characteristics of the drug, e.g. an exponential decay of each administered dosage. Historical dosages will have a smaller remaining effect than more recent dosages. Historical dosages could be estimated as long-term average using the techniques described above for computing a long-term metric of drug delivery. A new dosage could then be computed using a weighted combination of a long-term metric of delivered dosages and a medium and/or short term dosage measurement. In this example, the physiological variable being estimated is a residual drug effect, and the physiological condition or event used to estimate the physiological variable is the drug administrations or dosages delivered over time. A "sensed physiological signal" in this example is therefore a measurement of the drug delivery, which may be sensed or tracked by the IMD.

In FIG. 5, a long-term metric of drug delivery is initialized to a selected value, which may be a currently delivered dosage, at block 402. Upon detecting a need for drug administration at block 404, a residual drug metric is computed at block 406 using the long-term metric computed at block 406. A dosage is then computed at block 408 based on the residual drug metric and delivered. Initially, a dosage may be a nominal, minimal, or maximal dosage until enough dosages have been delivered to compute a dosage based on a formula for calculated a residual drug metric as described below. The dosage may be delivered in response to automatically detecting a pathological condition or worsening physiological condition based on sensed signals received by a sensing module 102 of IMD 10. In some embodiments, the need for drug administration may be detected as a patient or clinician command. The dosage may be delivered automatically by a therapy delivery module 104 including a drug delivery pump under the control of a control unit 106 of IMD 10.

The currently delivered dosage is used to update the long-term metric at block 410 by computing a weighted combination of the long-term metric and the current dosage. The weighted combination may be computed using the general formula given previously for a long-term metric, which includes a weighting of the previous long-term metric corresponding to a maximum number of dosages expected to occur during a decay period of the drug. In other words, the weighting of the previous long-term metric used in computing an updated metric may be based on a maximum number of dosages expected to be delivered during a response time over which the drug would decay.

At block 412, a medium-term drug delivery metric may be computed and may be an average of a predetermined number of the most recent administered dosages. The process then waits until a need for drug administration is detected and computes a residual drug metric at block 406. The residual drug metric may taken into account how long ago the most recent dosage was delivered. A metric of residual drug effects may be computed based on a weighted combination of the long-term metric, medium-term metric, and most recent delivered dosage. The metric of residual drug effect may be computed according to a formula of the general form given above for estimating a physiological variable from metrics of a physiological condition or event. In this case, the residual drug effect is computed from a long-term metric and medium term metric of drug delivery and a most recent dosage, each with appropriate weighting factors.

At block 408, a new dosage is computed based on the residual drug metric, which may include applying a scaling factor and offset to the residual drug effect metric, along with a maximum dosage limit. The coefficients and other constants used in computing a dosage may be based on fitting empirical data with a resolution needed according to particular drug characteristics. In this way, an appropriate dosage may be computed to maintain the patient within an acceptable total drug load without having to compute complex half-life behavior of multiple dosages over time.

Thus, a medical device system and associated method for computing an estimate of a physiological variable have been presented in the foregoing description with reference to specific embodiments. It is appreciated that various modifications to the referenced embodiments may be made without departing from the scope of the disclosure as set forth in the following claims.

The invention claimed is:

1. A medical device for computing an estimate of a physiological variable, the medical device comprising:
   a sensing module configured to receive a physiological signal and measure an event of the physiological signal;
   a memory configured to store a long-term metric of the event measurement, wherein the long-term metric corresponds to a time interval correlated to a response time of the physiological variable to changes in the event; and
   a control unit configured to:
   initialize a value of the long-term metric of the event measurement;
   update the long-term metric in the memory using a previous long-term metric of the event measurement and a current measurement of the event;
   detect a need for computing the physiological variable, wherein detecting the need for computing the physiological variable estimate comprises detecting a need for therapy delivery;
   compute the estimate of the physiological variable using the updated long-term metric;
   a therapy control unit configured to determine a therapy control parameter using the physiological variable estimate; and
   a telemetry module configured to transmit the determined therapy control parameter.

2. The device of claim 1, wherein the long-term metric is correlated to a centeredness measurement of the event over the response time.

3. The device of claim 1, wherein the memory stores a first weighting factor corresponding to the previous long-term metric and a second weighting factor corresponding to the current event measurement, the first weighting factor established based on an expected number of event measurements during the response time of the variable to a change in the event;
   the control unit configured to compute the estimate of the variable as a weighted combination of the previous long-term metric and the current measurement of the event.

4. The device of claim 3, wherein the first weighting factor corresponds to a maximum number of expected event measurements occurring during the response time.

5. The device of claim 1, wherein the control unit is further configured to:
   compute a medium-term metric using a predetermined number of measurements of the event;
   wherein computing the physiological variable estimate comprises computing a weighted combination of the updated long-term metric and the medium-term metric.

6. The device of claim 5, wherein the predetermined number of the event measurements is based on a minimum number of event measurements expected to occur in the response time of the physiological variable to a change in the event.

7. The device of claim 1, wherein computing the physiological variable estimate comprises approximating a non-linear response of the physiological variable as a function of the event by computing a weighted combination of the updated long-term metric, a medium term metric of the event computed from a predetermined number of recent event measurements, and a current measurement of the event.

8. The device of claim 1, further comprising:
   a therapy control unit configured to determine a therapy control parameter using the physiological variable estimate; and
   a therapy delivery unit controlled by the control unit to deliver the therapy using the determined therapy control parameter.

9. The device of claim 8, wherein detecting the need for therapy delivery comprises detecting a tachycardia,
   the therapy control parameter being an anti-tachycardia pacing interval,
   the physiological variable being an action potential duration computed using an updated long-term metric of cardiac cycle intervals,
   wherein the therapy delivery unit is controlled to deliver anti-tachycardia pacing pulses at the pacing interval computed using the estimated action potential duration.

10. The device of claim 1, further comprising a telemetry module configured to transmit the estimate of the physiological variable computed using the updated long-term metric.

11. The device of claim 1, wherein measuring the event comprises measuring
   a cardiac cycle interval;
   the physiological variable being an action potential duration computed using an updated long-term metric of cardiac cycle intervals.

12. The device of claim 1, wherein measuring the event comprises measuring a delivered dosage of a drug;
   the physiological variable being a residual drug effect computed using an updated long-term metric of delivered dosage.

13. A method for computing an estimate of a physiological variable in a medical device, the method comprising:
- enabling the medical device to sense a physiological signal;
- measuring an event of the physiological signal;
- initializing a value of a long-term metric of the event measurement, wherein the long-term metric corresponds to a time interval correlated to a centeredness measurement of the event over a response time of the physiological variable to changes in the event;
- updating the long-term metric in a memory of the medical device using a previous long-term metric and a current measurement of the event;
- detecting a need for computing the physiological variable, wherein detecting the need for computing the physiological variable estimate comprises detecting a need for therapy delivery;
- enabling a processor of the medical device to compute an estimate of the physiological variable using the updated long-term metric;
- computing a therapy control parameter using the physiological variable estimate; and
- transmitting the computed therapy control parameter.

14. The method of claim 13, further comprising establishing a first weighting factor corresponding to the previous long-term metric and a second weighting factor corresponding to the current event measurement, the first weighting factor established based on an expected number of event measurements during the response time of the variable to a change in the event;
- computing the estimate as a weighted combination of the previous long-term metric and the current measurement of the event.

15. The method of claim 14, wherein the first weighting factor corresponds to a maximum number of expected event measurements occurring during the response time.

16. The method of claim 13, further comprising transmitting the estimate of the physiological variable computed using the updated long-term metric.

* * * * *